US 6,549,645 B1

(12) United States Patent
Oikawa et al.

(10) Patent No.: US 6,549,645 B1
(45) Date of Patent: Apr. 15, 2003

(54) IMAGE PROCESSING METHOD AND APPARATUS ADAPTED FOR RADIOTHERAPY TREATMENT PLANNING USING DIGITALLY RECONSTRUCTED RADIOGRAPH

(75) Inventors: Michio Oikawa, Ebina (JP); Kenichi Kaneki, Nagareyama (JP); Yusuke Shimizu, Kashiwa (JP); Youichi Seto, Sagamihara (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/094,489

(22) Filed: Jun. 10, 1998

(30) Foreign Application Priority Data

Jun. 13, 1997 (JP) .............................. 9-156371

(51) Int. Cl.[7] ................................................ G06K 9/00
(52) U.S. Cl. ...................................... 382/132; 382/154
(58) Field of Search ................................ 382/128, 132; 324/309; 378/57, 65; 600/407; 606/130

(56) References Cited

U.S. PATENT DOCUMENTS

| 4,585,992 | A | * | 4/1986  | Maudsley et al. ........... 324/309 |
| 4,737,921 | A |   | 4/1988  | Goldwasser et al. |
| 5,151,856 | A | * | 9/1992  | Halmann et al. ............ 600/410 |
| 5,280,428 | A |   | 1/1994  | Wu et al. |
| 5,283,837 | A |   | 2/1994  | Wood |
| 5,368,033 | A | * | 11/1994 | Moshfeghi ................... 324/306 |
| 5,381,518 | A | * | 1/1995  | Drebin et al. ................ 345/421 |
| 5,471,990 | A | * | 12/1995 | Trisk .......................... 600/455 |
| 5,568,384 | A | * | 10/1996 | Robb et al. .................. 382/132 |
| 5,570,460 | A | * | 10/1996 | Ramanujam ................. 345/424 |
| 5,594,807 | A | * | 1/1997  | Liu ............................. 382/128 |
| 5,621,779 | A | * | 4/1997  | Hughes et al. ................ 378/65 |
| 5,740,225 | A | * | 4/1998  | Nabatame ..................... 378/65 |
| 5,760,781 | A | * | 6/1998  | Kaufman et al. ............ 345/424 |
| 5,937,083 | A | * | 8/1999  | Ostuni ......................... 382/131 |
| 5,947,981 | A | * | 9/1999  | Cosman ....................... 128/869 |
| 6,219,061 | B1 | * | 4/2001 | Lauer et al. ................. 345/419 |

FOREIGN PATENT DOCUMENTS

| EP | 0 365 141 A2 | 4/1990 |  |
| EP | 0506302 A1 | * 9/1992 | ........... G01R/33/56 |
| EP | 0 506 302 A1 | * 9/1992 | ........... G01R/33/56 |
| EP | 0 568 351 A1 | 11/1993 |  |
| EP | 0 621 546 A2 | 10/1994 |  |
| JP | 8-164217 | 6/1996 |  |

OTHER PUBLICATIONS

Galvin et al, The Use of Digitally Reconstructed Radiographs for Three–Dimensional Treatment Planning and CT–Simulaion, Jun. 23, 1994, pp. 935–942.*

J. Galvin et al., "The Use of Reconstructed Radiographs for Three–Dimensional Treatment Planning and CT–Simulation", Int. J. Radiation Oncology Biol. Phys., vol. 31, No. 4, pp. 935–942, 1995.

* cited by examiner

Primary Examiner—Timothy M. Johnson
(74) Attorney, Agent, or Firm—Antonelli, Terry, Stout & Kraus, LLP

(57) ABSTRACT

Three-dimensional data is generated by measuring an affected part using a computed tomography unit. Then, color information is allocated so as to correspond to voxel values of the three-dimensional data, and the allocated color information is added up along a ray irradiated from a radiation source. As a result, a digitally reconstructed radiograph (DRR) is generated and displayed.

36 Claims, 11 Drawing Sheets

VOXEL VALUE RANGE

FIG.5A
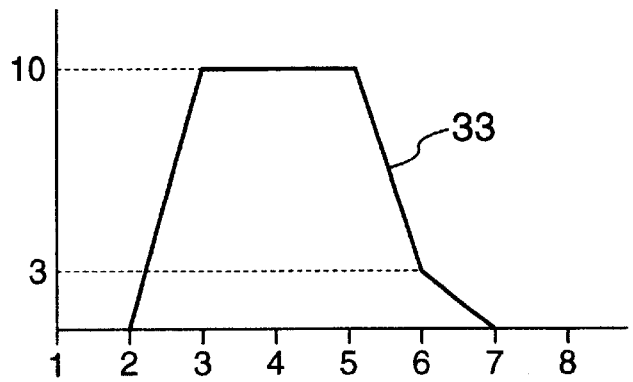
2-DIMENSIONAL DATA
FIG.5B
FIG.5C
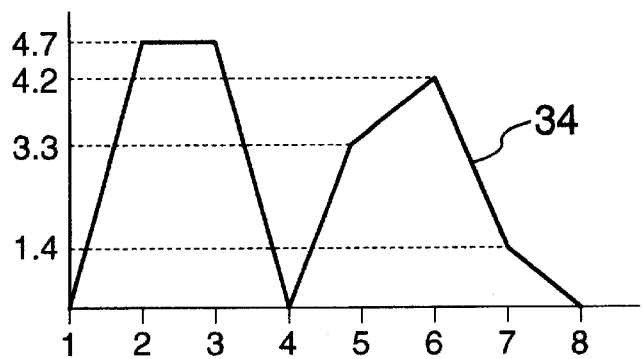
EDGE-PROCESSED DATA
FIG.5D

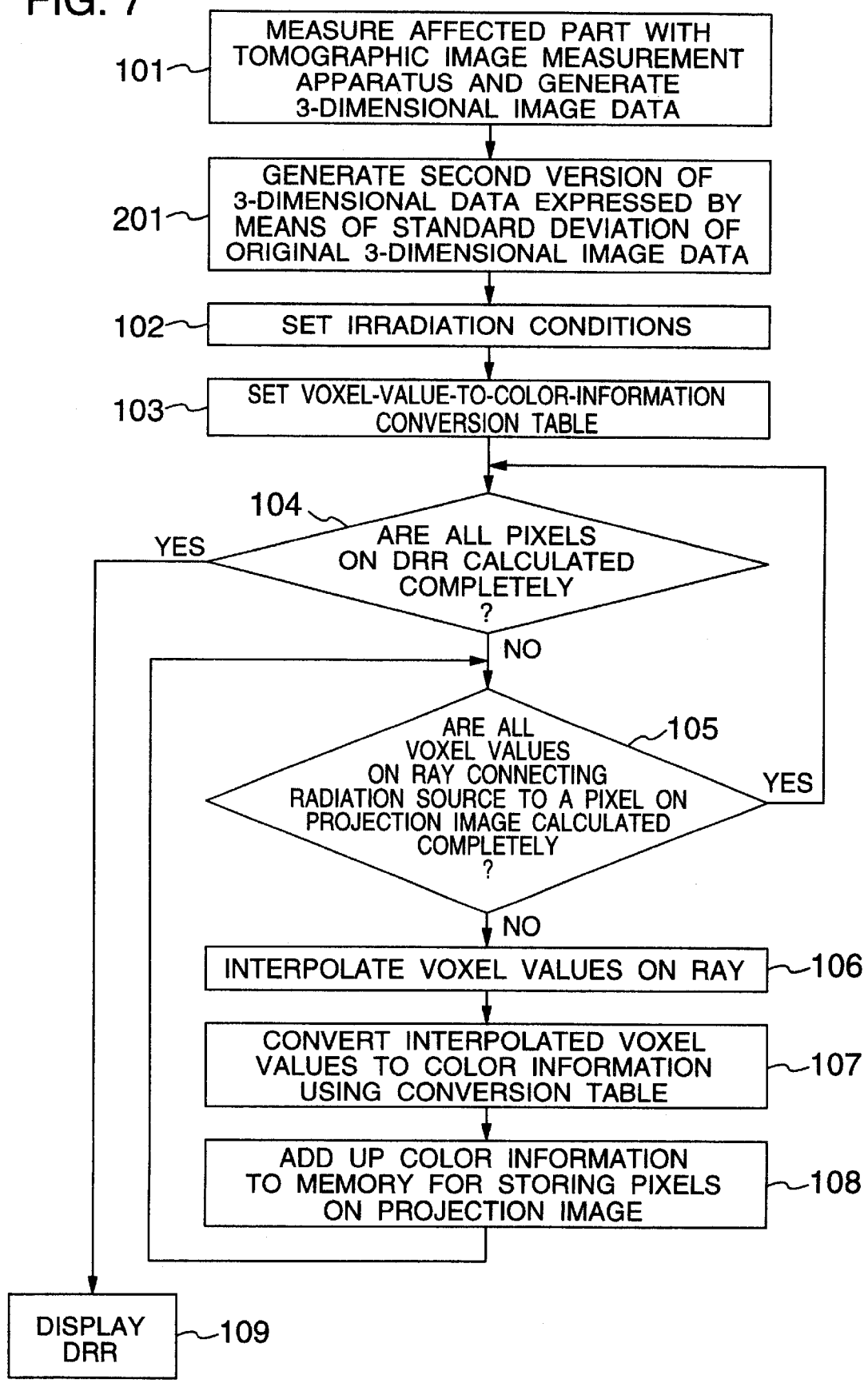

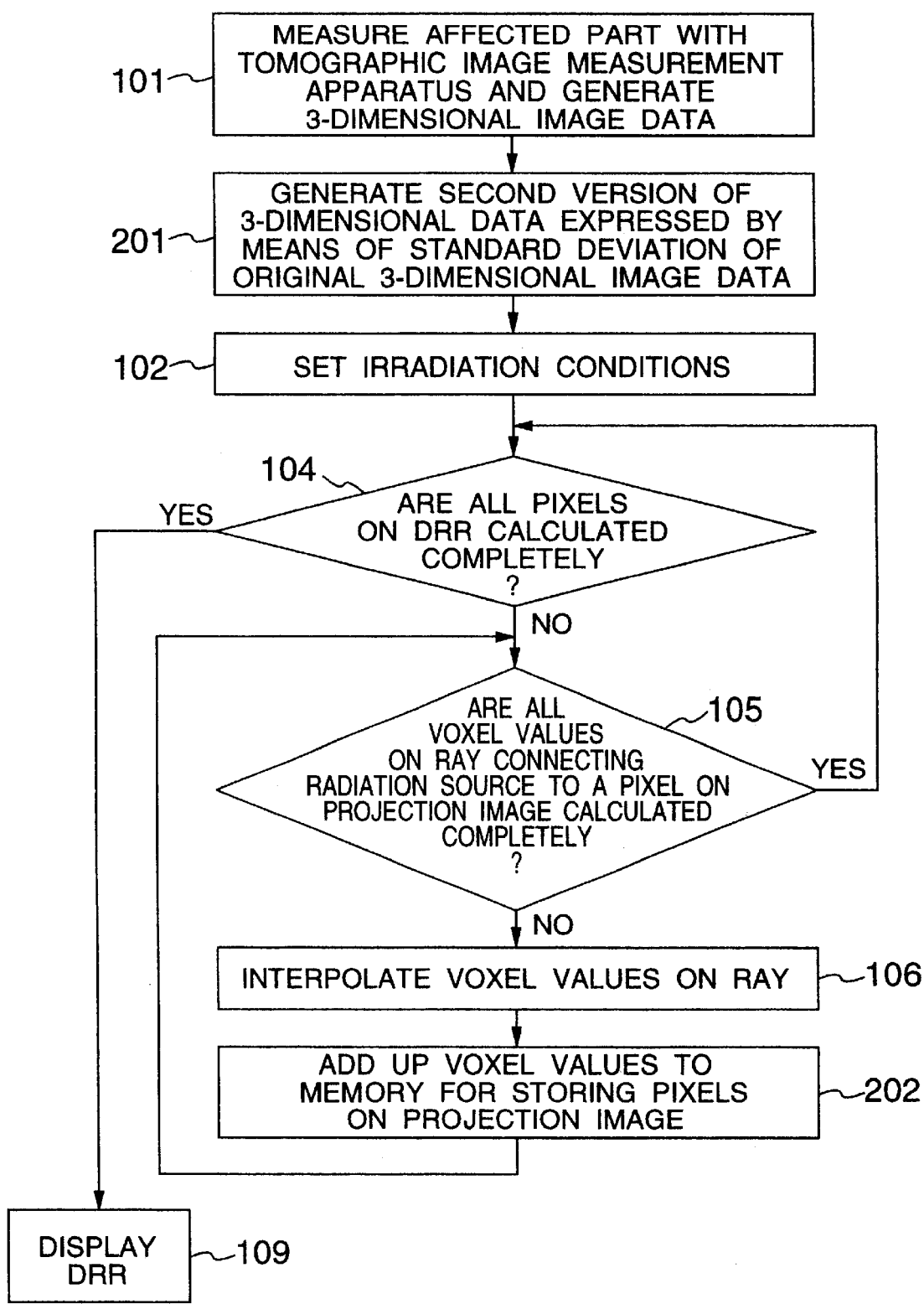

FIG. 11A

| 1 | 14 | 2 | 15 | 3 |
|---|----|---|----|---|
| 20 | 10 | 21 | 11 | 22 |
| 4 | 16 | 5 | 17 | 6 |
| 23 | 12 | 24 | 13 | 25 |
| 7 | 18 | 8 | 19 | 9 |

| 1 | 2 | 3 |
|---|---|---|
| 4 | 5 | 6 |
| 7 | 8 | 9 |

| 1 | 2 | 3 |
|---|---|---|
| 10 | 11 | |
| 4 | 5 | 6 |
| 12 | 13 | |
| 7 | 8 | 9 |

| 1 | 14 | 2 | 15 | 3 |
|---|----|---|----|---|
| 10 | | 11 | | |
| 4 | 16 | 5 | 17 | 6 |
| 12 | | 13 | | |
| 7 | 18 | 8 | 19 | 9 |

| VOXEL VALUE RANGE | | COLOR INFORMATION | | |
|---|---|---|---|---|
| MINIMUM VALUE | MAXIMUM VALUE | R | G | B |
| -1000 | -100 | 128*(V+1000)/900 | 128*(V+1000)/900 | 128*(V+1000)/900 |
| -99 | 99 | 200 | 0 | 0 |
| 100 | 1000 | 0 | 255*(V-100)/900 | 255*(V-100)/900 |

IMAGE PROCESSING METHOD AND APPARATUS ADAPTED FOR RADIOTHERAPY TREATMENT PLANNING USING DIGITALLY RECONSTRUCTED RADIOGRAPH

BACKGROUND OF THE INVENTION

The present invention relates to an image processing method and an apparatus that prepare treatment planning based on three-dimensional data obtained by making measurements on a patient using an X-ray computed tomography (CT) unit in treating diseases such as cancer with radiation. More specifically, the present invention is directed to an image processing method and apparatus adapted for radiotherapy treatment planning using digitally reconstructed radiographs (DRRs), which are permeation images generated from three-dimensional data obtained from a tomographic image measurement apparatus.

Treatment methods involving injection of beams of radiation such as X-rays and beams of protons onto a focus portion such as cancer are considered effective. To give a patient such a treatment, preliminary treatment planning must be prepared. A radiotherapy treatment is generally given under the following procedure.

First, part of a patient body including an affected part is measured using an apparatus such as an X-ray CT unit. The affected part is specified from the measured data, and its position and size are grasped. Then, the isocenter is set to the affected part, and conditions such as the direction of irradiation, number of injections and range of irradiation are simulated and adjusted so that radiation can be focused onto the affected part as closely as possible. Then, based on the results of the simulation and adjustment, markings are made on the patient body. Thereafter, the patient is requested to go to the radiotherapy treatment unit, positioned on the unit in accordance with the markings, and given the treatment.

At the time of the aforementioned simulation, a method of preparing treatment planning using DRRs is available. The DRR is a photographic image obtained by projecting onto a plane the pixels of data produced by a computed tomography unit such as an X-ray CT unit (these pixels will hereinafter be referred to as "voxels") using radially expanding rays that are irradiated from a radiation source.

The treatment planning using DRRs provides the advantage that correct simulations can be made by calculating the radiograph of an affected part based on the same paths as those of the radiation beam provided by the actual treatment unit.

However, simple calculation of a radiograph imposes the problem that the transmitted body structure is hard to grasp. The following literature provide some (1) J. Galvin et al., "The Use of Digitally Reconstructed Radiographs for Three-Dimensional Treatment Planning and CT-Simulation", Int. J. Radiation Oncoloay Biol. Phys., Vol. 31, No. 4, pp. 935–942, 1995, and (2) JP-A-8-164217.

Such literature disclose DRR generation methods that use a lookup table for making CT value conversions to highlight a bone area serving as a landmark when a radiograph is calculated. The CT value conversions are made using a bone window or the like.

However, the conventional techniques are successful in improving the contrast of the bone area, but unsuccessful in generating a DRR having an area of interest highlighted more clearly. If clear highlighting is implemented, the user can prepare a more accurate treatment design. Further, while an exemplary method disclosed in JP-A-8-164217 involves an edge process to project an area such as a bone area clearly, the edge process is not specifically described. Thus, an effective edge process to enhance the contour using treatment data from an X-ray CT unit or the like must be developed.

Moreover, for treatment planning, measurements must be made with respect to the size of a target tumor and the size of an irradiation range. Since a DRR is a projected image formed by radially expanding rays, such measurements cannot be made on the DRR.

Furthermore, it takes much time to generate a DRR. Therefore, for interactive data processing, a high-performance computer is required, and this has prevented interactive processing with a low-performance computer.

SUMMARY OF THE INVENTION

To overcome the aforementioned problems, the present invention provides a unit for allocating color information so as to correspond to pixel values of three-dimensional data that is measured by an X-ray CT unit or the like, and allows a DRR to be generated by projecting the data using color information converted from the pixel values. In addition, the present invention provides a method of subjecting three-dimensional data that is measured by an X-ray CT unit or the like to an edge process based on a standard deviation, and allows a DRR to be generated by projecting the thus edge-processed three-dimensional data.

In the present invention, a position for projecting a DRR may be on a flat plane which includes an isocenter and which is perpendicular to a line connecting the isocenter to a radiation source. In the present invention, the user may specify the number of pixels and resolution of a DRR, and the sampling interval of voxels on a ray connecting a pixel on the DRR and the radiation source. Further, intermediate images of low resolution may be displayed until a final DRR is displayed.

As described above, the image processing method according to the present invention allows the user to clearly display and easily grasp an area of interest such as a bone structure and the contour and shape of organs by means of an edge process when the user prepares treatment planning based on a DRR, which is a radiograph, consisting of three-dimensional data gathered from a computed tomography unit such as an X-ray CT unit before a radiotherapy treatment is given to a patient.

Moreover, the image processing method according to the present invention allows the user to measure data on a flat plane of a DRR including the isocenter of an area of utmost interest when data such as the size of a target tumor and the range of irradiation are measured. Furthermore, the method allows the user to select image quality and speed. Since the user can roughly grasp the condition of the area of interest before obtaining a final, high-resolution DRR, the user is allowed to process data interactively by, e.g., changing the direction of irradiation in order to generate the final DRR with improved resolution and increased number of pixels.

BRIEF DESCRIPTION OF THE DRAWINGS

FIGS. 5A to 5D are diagrams showing an exemplary edge process based on a standard deviation using two-dimensional data;

FIG. 7 is a flowchart of an image processing method for executing an edge process, which is an embodiment of the present invention;

FIG. 8 is a flowchart of an image processing method for executing an edge process, which is another embodiment of the present invention;

FIGS. 11A to 11D are diagrams showing an example in which a high-quality DRR is displayed on a step-by-step basis;

FIG. 12 is a diagram showing an exemplary table for allocating color information.

DESCRIPTION OF THE PREFERRED EMBODIMENTS

Embodiments of the present invention will now be described in detail with reference to the drawings.

Figure 1:
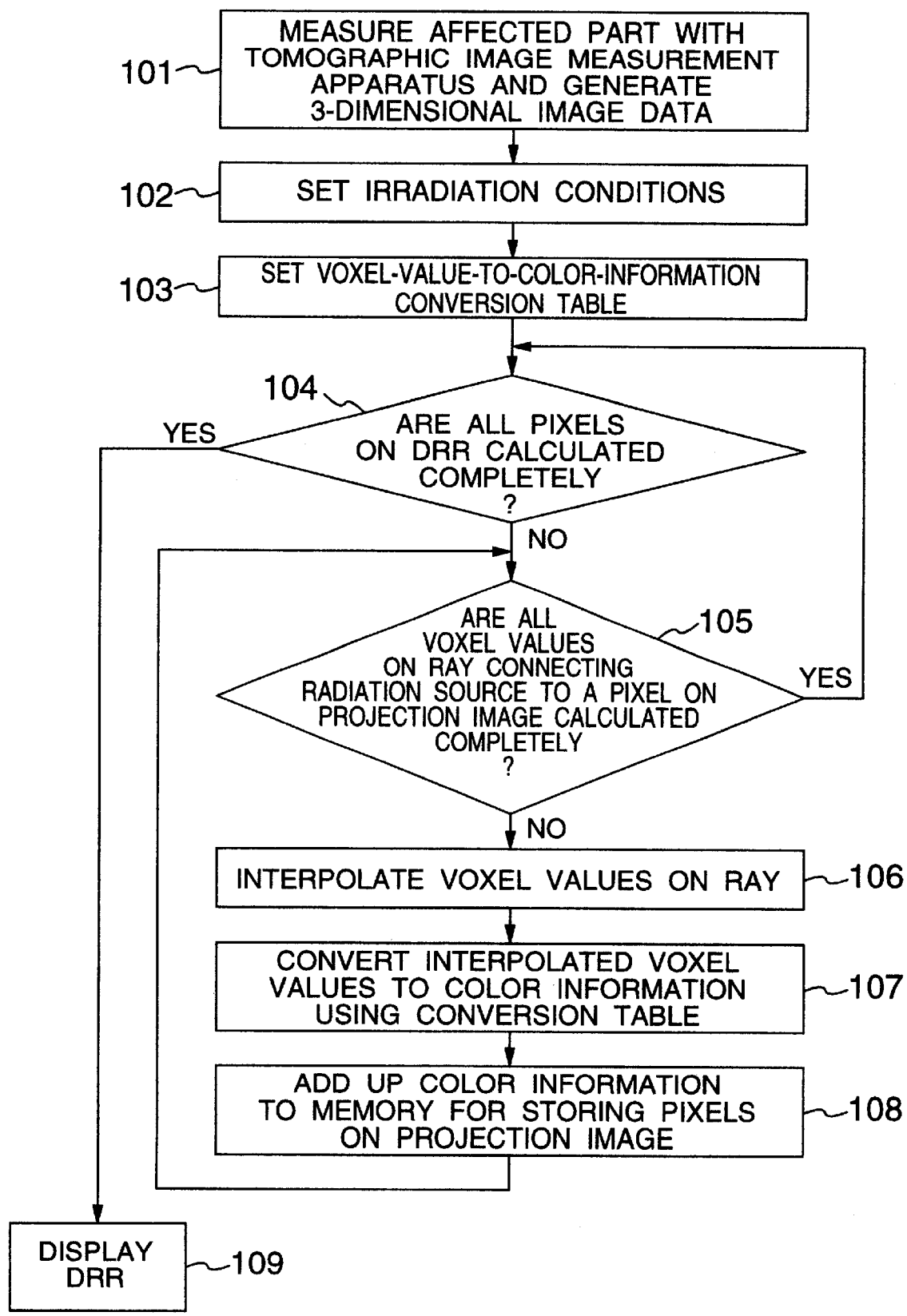
FIG. 1 is a flowchart of an image processing method, which is an embodiment of the present invention.

FIG. 1 is a flowchart showing a radiograph generation method, which is an embodiment of an image processing method to which the present invention is applied. The flowchart will be described with reference to the process of a radiotherapy treatment shown in FIG. 2.

Figure 2:
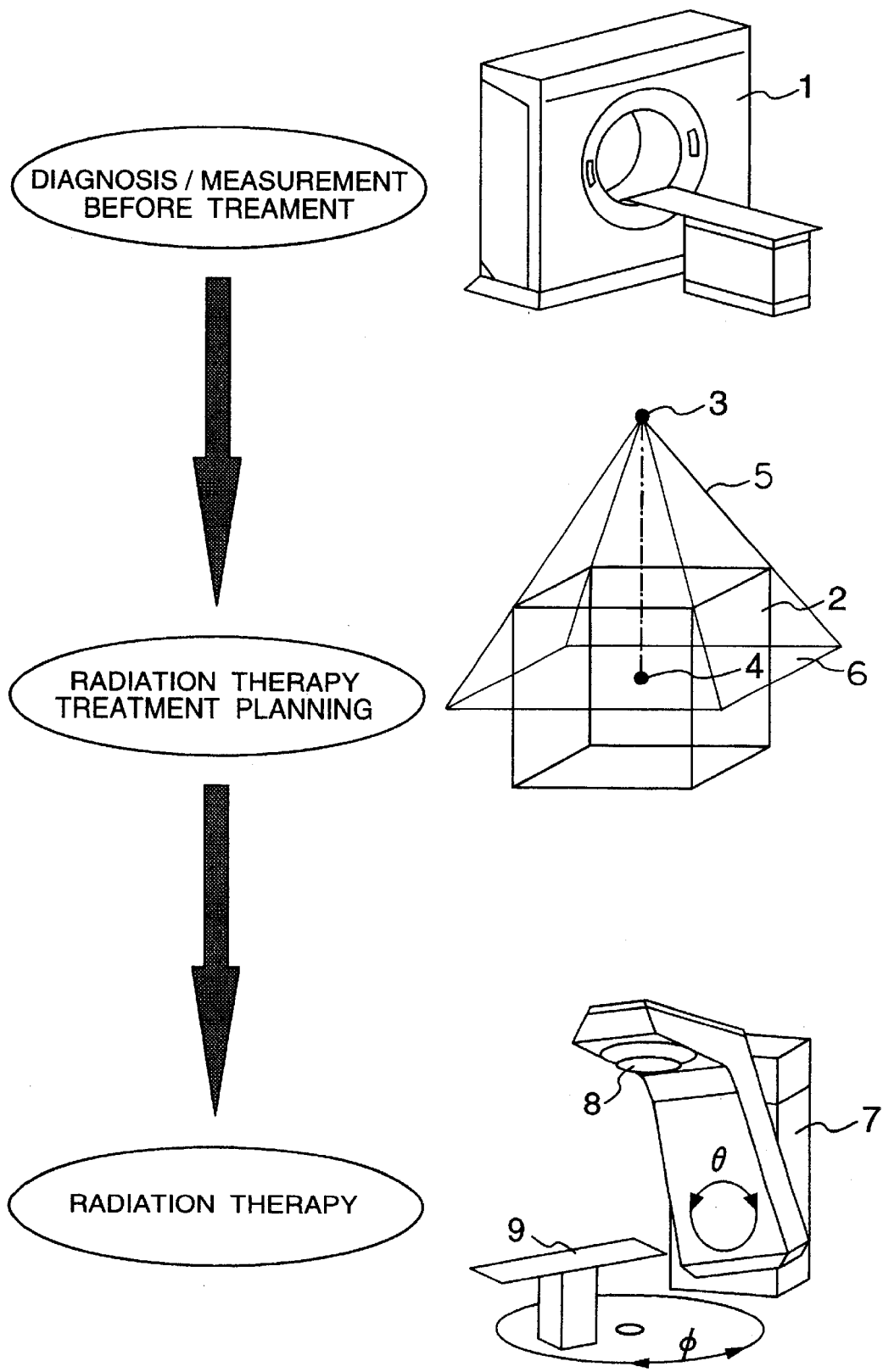
FIG. 2 is a diagram showing the entire process of radiotherapy treatment planning.

The image of an area including an affected part is made using a tomographic image measurement apparatus 1 such as an X-ray CT unit shown in FIG. 2 before a patient is subjected to a treatment, and thus three-dimensional image data 2 is prepared (Step 101). Then, irradiation conditions necessary for treating the patient with a radiotherapy treatment unit 7 are set Step 102). The irradiation conditions include a position of a radiation source 3, an isocenter position 4 onto which radiation is focused, a degree of expansion of a radiation beam 5 and so forth. The three-dimensional data 2 is projected onto a DRR plane 6 which is set so as to coincide with a plane including the isocenter 4. The position of the radiation source 3 is rotatable about the specified isocenter 4 by rotating and moving a gantry 8 and a table 9 of the radiotherapy treatment unit 7.

Successively, to highlight an area of interest, a color information conversion table corresponding to voxel data (hereinafter referred to as "voxel values") such as CT values is set (Step 103). The table contains color information corresponding to a range of voxel values in terms of RGB ratio, as shown, e.g., in FIG. 12, where V is the voxel value. The table shown in FIG. 12 can allocate values linearly within the range of voxel values. In this example, the voxel values ranging from −1000 to −100 are converted to the color information of gray having gradations ranging from 0 to 128, the voxel values mainly indicating vascular areas and ranging from −99 to 99 are converted to the color information of red having a gradation of 200, and the voxel values mainly indicating bones and ranging from 100 to 1000 are converted to the color information of yellow having 0 to 255 gradations.

Figure 3A:
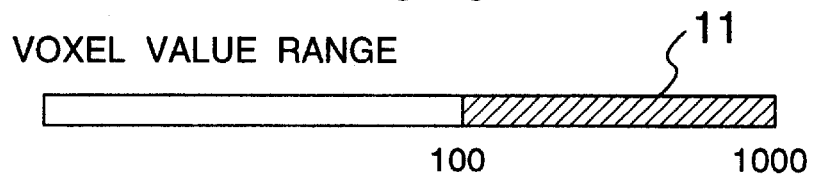
FIG. 3A is a diagram showing an exemplary unit for specifying a range of voxel values to which color information is allocated.
Figure 3B:
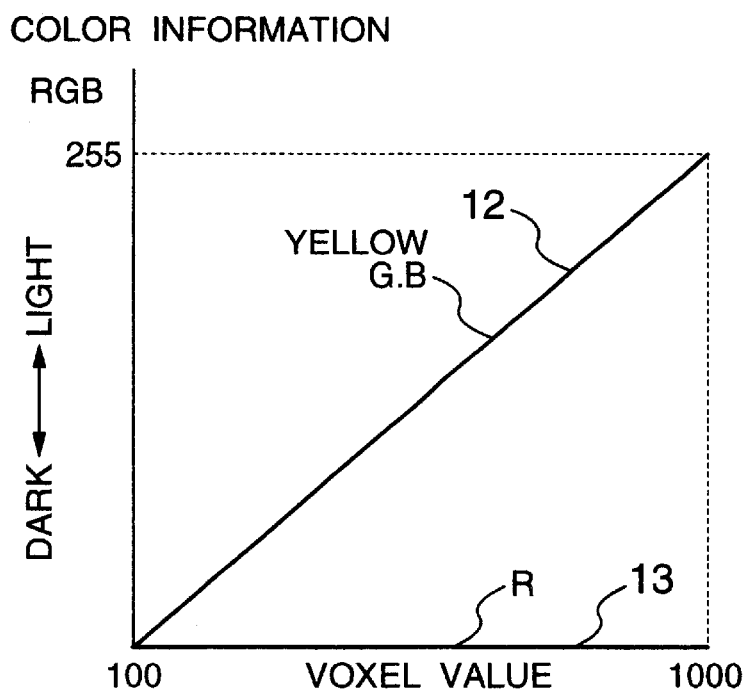
FIG. 3B is a diagram showing an exemplary unit for allocating the color information.

An embodiment of a method by which a user specifies the color information table is shown in FIGS. 3A and 3B. First of all, as shown in FIG. 3A, the user specifies a range 11 for which color information is obtained. The range 11 can be selected by, e.g., dragging both ends of a target range 11 using a mouse. Then, as shown in FIG. 3B, the user prepares the color information table corresponding to the selected voxel value range. In this example, the user specification is such that colors G and B change as shown by a line 12 and that color R remains at 0 as shown by a line 13. These lines are specified by, e.g., dragging the ends of each line using the mouse. Through these operations, the color information table such as shown in FIG. 12 can be prepared automatically. Then, a DRR, which is a radiograph, is produced by sequentially calculating all the pixels on the DRR.

These lines are specified by, e.g., dragging the ends of each line using the mouse. Through these operations, the color information table such as shown in FIG. 12 can be prepared automatically. Then, a DRR, which is a radiograph, is produced by sequentially calculating all the pixels on the DRR. First, assuming a ray connecting a pixel on the DRR and the radiation source, voxel values on such ray are interpolated (Step 106 (since Steps 104 and 105 result in "NO" in the first operation, so that the process proceeds to step 106)). The interpolated voxel values are converted to color information by means of the color information table set in Step 103 (Step 107). Successively, the converted color information is added up to a memory for storing the pixel values of the DRR (Step 108). The pixel value storing memory is initially cleared, and the color information corresponding to the voxel values on the ray is sequentially added up. The addition is made on a color component (R, G, B) basis. This calculation is made for all the voxel values in the three-dimensional data present on the ray (Step 105). Upon completion of the calculation for all the pixels on the DRR (Step 104), the calculated DRR is displayed (Step 109). The DRR may, thereafter, be printed or stored in a hard disk, etc. Thus, this method, in which different areas are displayed in different colors, allows the user to discern bones, organs, tumors and the like with ease.

According to the aforementioned method, different colors can be used to display different areas that are specified by respective voxel value ranges, and this allows the user to highlight areas of interest in preparing a treatment design.

Method of Specifying Voxel Value Range

Figure 4A:
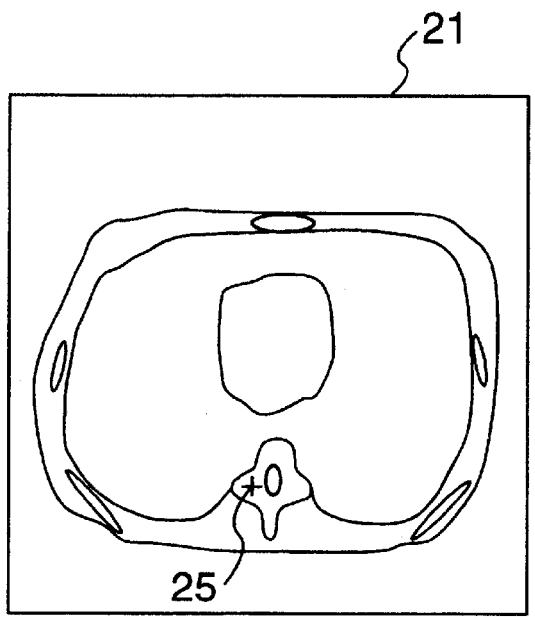
FIGS. 4A to 4C are diagrams showing another exemplary unit for specifying a range of voxel values to which color information is allocated.
Figure 4B:
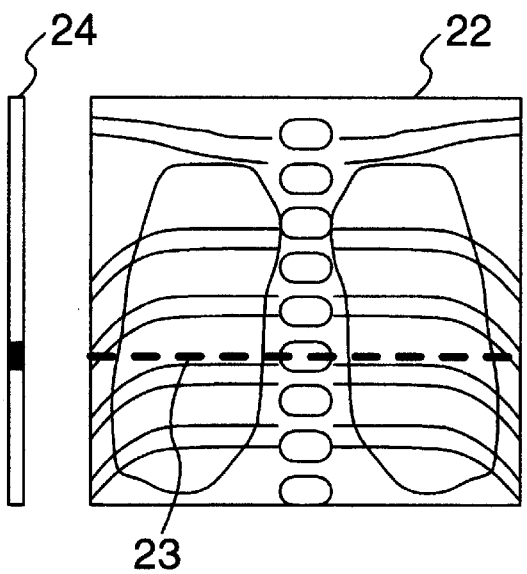
Figure 4C:
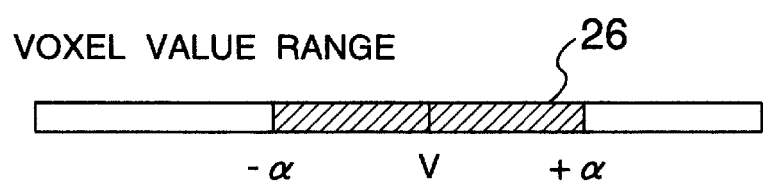

Another embodiment of a color information specifying method will be described with reference to FIGS. 4A to 4C.

Using three-dimensional data obtained by a tomographic image measurement apparatus before treatment, a sliced image 21 is displayed. The position of the displayed cross-sectional image is indicated in the form of a line 23 on a scanogram 22 so that the user can locate the position. The position of the sliced image 21 can be moved by dragging the line 23 with the mouse or the slicing position can be moved with a slider 24.

Then, a single point in an area to be highlighted is specified on the sliced image 21 using a pointer 25. The voxel value V of the specified point is retrieved, and the retrieved value V is set as the central value of a voxel value range 26, so that the range 26 covering an interval of ±α from the central value V can thereafter be set for preparing a color information table. While a predetermined initial value is used as α, the interval α can be altered by dragging either the upper end or lower end of the color information setting range with the mouse. Once the voxel value range is specified in this way, the color information table is prepared based on the method described with reference to FIGS. 3A and 3B. This method allows the user to visually specify the voxel values of the area to be highlighted.

Further, if the user specifies a voxel value range and displays the sliced image 21 using only the voxels contained in the specified voxel value range, the voxel value range specifying operation becomes easier.

Still further, instead of specifying the area to be highlighted with a single point, such area may be specified by determining the voxel value range for color information specification based on the maximum and minimum values of the voxel values contained in a rectangular area.

Standard Deviation

A display method by which a structure such as a bone can be easily identified on a DRR by smoothly enhancing the contour of the structure such as a bone will be described with reference to FIGS. 5A to 5D. To enhance the contour of an image, an edge process may be performed so that a voxel value at a position where there is an abrupt voxel value change is converted into a higher value than voxel values adjacent to such voxel value. An embodiment of the present invention in which a DRR is prepared using edge-processed data will be described below. Since techniques based on differential analyses produce data having plenty of noise with high-frequency components emphasized, a technique based on a standard deviation is used in this embodiment to express desired voxel values.

A standard deviation σ can be given by equation 1, assuming that the number of voxels within a block is n and that the density of a voxel i is $v_i$.

Equation 1

$$\sigma = \sqrt{\frac{1}{n}\sum_{i=1}^{n} vi^2 - \left(\frac{1}{n}\sum_{i=1}^{n} vi\right)^2}$$

FIGS. 5A to 5D show the results of an edge process that is performed with a block size of 3×3 using two-dimensional data. The 3×3 block is the minimum unit for performing the edge process, and the two-dimensional data is used for a concise description. FIG. 5C shows the results 32 of an edge process performed by calculating a 3×3-block-based standard deviation for an area surrounded by the thick line in two-dimensional data 31 shown in FIG. 5A. The graphs in FIGS. 5B and 5D show changes in the data. The graph 33 shows a change in the original data surrounded by the thick line and the graph 34 shows a change in the edge-processed data. The numerals given on the horizontal axes of the graphs 33 and 34 correspond to the numerals superscribed on the original data surrounded by the thick line.

As can be seen from the graph 33, an edge in the original data 31 surrounded by the thick line is assumed to be located between the second and third pixels from the left. It can be seen from the edge-processed graph 34 that the contour is enhanced in the edge-processed data 32 because this edge is expressed by a high value between the second and third pixels from the left in the edge-processed graph 24. Further, there is another edge between the fifth and sixth pixels from the left in the original data 31. This edge, having a smaller density difference than the first edge, is expressed by a smaller value between the fifth and sixth pixels from the left in the edge-processed graph 34. Another edge between the sixth and seventh pixels from the left in the original data 31, having a further smaller density difference, is expressed by a further smaller value between the sixth and seventh pixels from the left in the edge-processed graph 34.

As in the aforementioned example, the edge-processed data is obtained by converting the original data as if the edge were present between voxels of the original data, i.e., between the second and third pixels of the original data. As a result, the contour is extended by one pixel. The conversion is performed so that the edge-processed voxels 2 and 3 represent an edge. However, this technique provides smoothing effects, which reduces noise and hence allows the contour of the structure such as a bone to be enhanced satisfactorily.

The edge process described in terms of two-dimensional data shown in FIGS. 5A to 5D can be applied directly to the horizontal and vertical directions of three-dimensional data.

Figure 6:
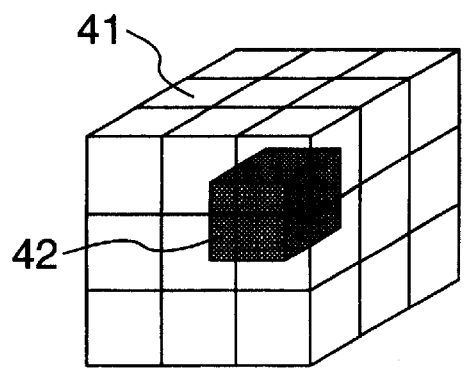
FIG. 6 is a diagram showing an exemplary block for calculating a standard deviation for three-dimensional data.

Three-dimensional data is subjected to an edge process in the following way. When a standard deviation is calculated using a 3×3×3 block 41 around a voxel 42 that is subjected to an edge process as shown in FIG. 6, satisfactory results can be obtained. It should be noted that when the aforementioned block is used, the edge process cannot be performed on the voxels on the outermost sides of the three-dimensional data. However, the effect is negligible since these voxels represent a small area in comparison with the total amount of data.

The edge-processed three-dimensional data is the edge-enhanced data in which portions of the original three-dimensional image with their densities drastically changed, i.e., edge portions are enhanced.

FIG. 7 is a flowchart, which is an embodiment of the present invention. The flowchart presents a process using an edge process and a color information conversion table. The process steps identical to those shown in FIG. 1 are denoted by the same step numbers.

In FIG. 7, a standard deviation a of the three-dimensional image data measured by a tomographic image measurement apparatus is calculated by the equation 1, and a second version of three-dimensional data is obtained by expressing the original three-dimensional image data using a in Step 201. In subsequent steps, the image process is performed using the second version of three-dimensional data.

Step 201 may be performed immediately after Step 102 or immediately after Step 103.

FIG. 8 shows another embodiment of a flowchart showing an edge process. The flowchart of FIG. 8 is distinguished from that of FIG. 7 in that the color information conversion table is not used. Therefore, Steps 103 and 107 in the flowchart of FIG. 7 are eliminated, and Step 202 replaces Step 108. In Step 202, voxel values are added up to a memory for storing pixels on a projected image. Other steps are identical to those of FIGS. 1 and 7.

Position of DRR Plane

Figure 9:
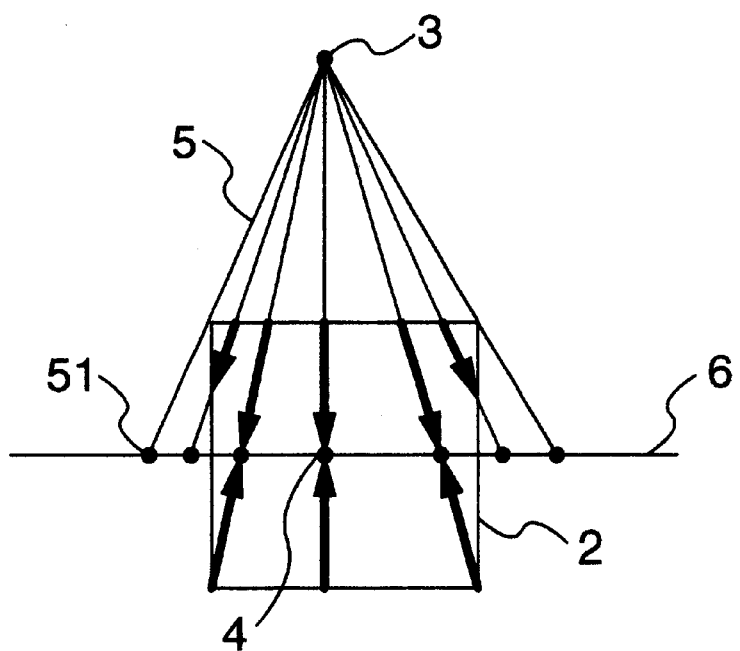
FIG. 9 is a diagram showing an exemplary projection made by setting a DRR plane at a position including an isocenter.

An embodiment of a method of projecting a DRR onto a plane passing through an isocenter will be described with reference to FIG. 9. The DRR may be prepared from non-edge-processed voxel data or from edge-processed voxel data. FIG. 9 is a cross section taken from a diagram showing the treatment planning of FIG. 2. The DRR plane 6 is set so as to coincide with a plane that includes the isocenter 4. The three-dimensional data 2 is projected onto the DRR plane 6 through the radiation beam 5 from the radiation source 3. The three-dimensional data 2 is added up and projected in both forward and backward directions as indicated by the arrows. That is, all the voxels in the three-dimensional data 2 present on a ray connecting the radiation source 3 to a pixel 51 on the DRR plane 6 are added up and projected. The voxel values are projected after being converted into color information using the color information conversion table shown in FIG. 12. However, when the edge-processed voxel data is used, the color information conversion table is not necessarily used. The DRR calculation method includes an image-order approach in which a DRR is calculated in the order of pixels, or an object-order approach in which a DRR is calculated in the order of three-dimensional data.

According to the aforementioned embodiment, the projected position of the DRR is on a plane including the isocenter. Since voxels which are remoter from the radiation source than the projected area and considered invalid in ordinary projections are projected, all the three-dimensional data can be visualized as the DRR. If the user wishes to generate a DRR in which only an area of interest is focused, all the data may not necessarily be visualized by limiting the area for calculation.

Further, the isocenter is usually set to the center of an affected part to be treated, and the range of irradiation is often set on a plane including the isocenter. Thus, in this embodiment, the irradiation range is displayed on a DRR by setting the pixel size of the DRR to coincide with the minimum value of the voxel size. As a result, the image of the affected part on the DRR becomes as big as the actual affected part. Hence, the DRR on the plane including the isocenter that is the center of an area of interest allows the user to make simulations easily.

Specification of Resolution

Figure 10:
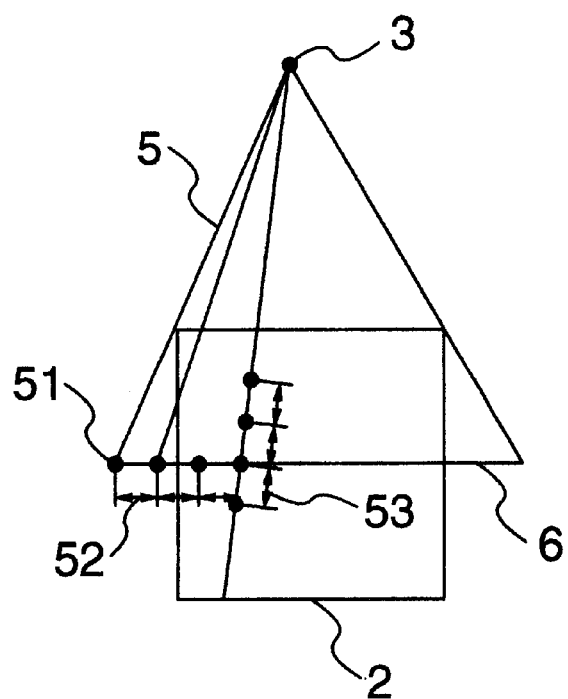
FIG. 10 is a diagram showing an example in which the number of pixels and resolution of a DRR, and a sampling interval of voxels on a ray connecting a pixel on the DRR to a radiation source are specified.

An embodiment of a method of improving the quality and speed of image forming operation by specifying the number of pixels and resolution will be described with reference to FIG. 10. Similarly to FIG. 9, FIG. 10 shows how a DRR is generated in the form of a cross section. In this case also, the DRR can be generated by using a color information conversion table and an edge process.

First, the resolution (pixel size) 52 and number of pixels of a DRR are specified. A value equal to the resolution (voxel size) of the three-dimensional data is set as an initial value (the finest resolution value is set in case of that the voxel size has different lengths), and such number of pixels as to allow all the three-dimensional data as to be projected (such number can be obtained from the radiation source, isocenter position, number of three-dimensional data voxels, resolution, and the like) is specified. Then, a sampling interval 53 on the ray connecting the radiation source 3 to the pixel 51 is specified. The value equal to the resolution of the DRR is specified as an initial value. Using the aforementioned initial values, the DRR corresponding to the quality of the three-dimensional data can be calculated.

If the user wishes to save calculation time, the number of pixels of the DRR can be reduced, or the sampling interval between voxels on the ray connecting the radiation source to the pixel is increased. As a result, the DRR can be calculated faster. If the number of pixels of the DRR is reduced without changing the resolution, the projection range is reduced, but the image quality remains unchanged. On the other hand, if not only the number of pixels is reduced but also the resolution is reduced accordingly, the image quality is impaired, but the projection range remains unchanged. The above similarly applies to the sampling interval between voxels on the ray. Further, if the user wishes to improve the image quality, the resolution of the DRR may be increased, or the sampling interval between voxels on the ray may be reduced.

As described above, the aforementioned embodiment allows calculation speed and image quality to be controlled in accordance with the usage of an image and the capacity of a computer.

Improvement of Interactivity

It takes time to generate a DRR. A solution to this problem is to improve interactivity by increasing the speed of generating a DRR in nominal terms. An embodiment of a method of implementing such high-speed operation will be described with reference FIGS. 11A to 11D. FIGS. 11A to 11D show a method in which calculations for generating a 5×5-pixel-based DRR are made in four steps and the calculated image is displayed every time the calculation is made. In this case also, the DRR can be generated by using a color information conversion table and an edge process.

Let us assume that a final DRR 61 is obtained through calculations. The numbers on the image are allocated to the respective pixels constituting the image, and indicate the order in which the pixels are calculated.

First, pixels 1 to 9 are calculated every other pixel in both horizontal and vertical directions. A first-step DRR 62 is generated from the initially calculated nine pixels, and the generated DRR 62 is displayed. The first DRR is displayed with the skipped pixel values (e.g., 14, 20, 10) represented as the calculated pixel values (e.g., 1) (FIG. 11B). Then, pixels 10 to 13, each being located at a position one pixel moved in both horizontal and vertical directions from the initially calculated pixel, are calculated. A second-step DRR 63 is generated using the calculated thirteen pixels and displayed. In this case, the pixels on the left of the pixels 10 to 13 are displayed as the same values (FIG. 11C). Then, pixels 14 to 19, each being located at a position one pixel moved in the horizontal direction from the initially calculated pixel, are calculated to generate and display a third-step DRR 64 using the nineteen pixels (FIG. 1D). Finally, the remaining pixels 20 to 25 are calculated to generate and display the final DRR 61 (FIG. 11A).

According to the aforementioned method, the user can grasp the outline of the DRR with the images 62, 63 and 64 in the intermediate steps sequentially displayed before all the pixels of the final DRR 61 are completely calculated. Thus, interactivity can be improved. The total time required for completing all the calculations, although a small time to generate the intermediate images is included, is substantially the same as that required in the method in which a DRR is displayed after all the pixels are directly calculated.

Figure 13:
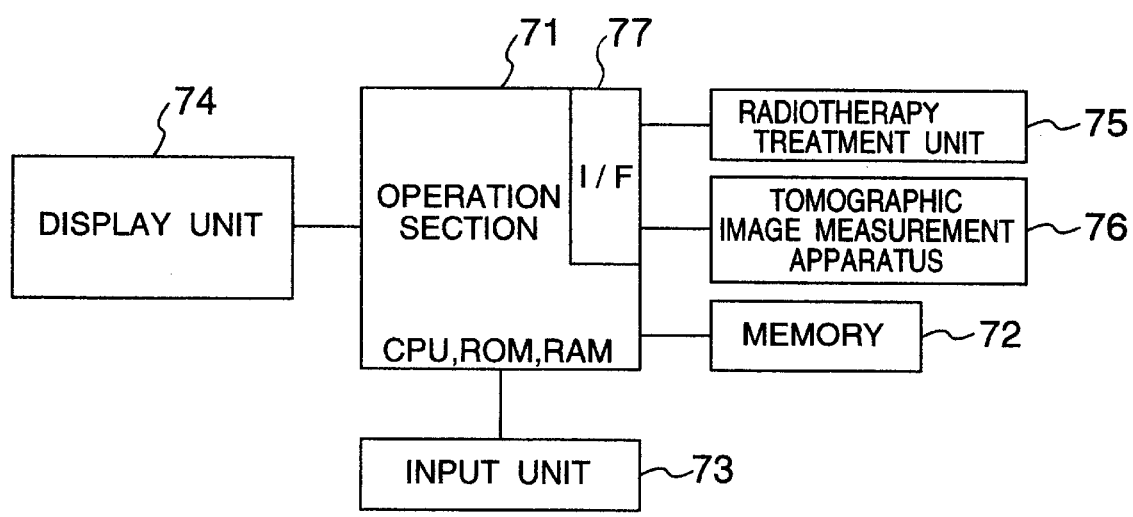
FIG. 13 is a block diagram showing an image processing apparatus, which is an embodiment of the present invention.

FIG. 13 is a block diagram showing an exemplary image processing apparatus that embodies the image processing method of the present invention. The image processing apparatus comprises an operation section 71, a memory 72, an input unit 73, a display unit 74, a radiotherapy treatment unit 75 and a tomographic image measurement apparatus 76. The operation section 71 includes a CPU, a ROM and a RAM and executes various processes such as a process for calculating a DRR using a color information conversion table and three-dimensional data subjected to a standard-deviation process. The memory 72 stores three-dimensional image data, edge-processed data, a color information conversion table such as shown in FIG. 12, DRR data and the like. The input unit 73 is a device such as a keyboard and a mouse. The display unit 74 displays an image that is digitally reconstructed by calculation. The radio-therapy treatment unit 75 is connected to the image processing apparatus through an interface section 77. The tomographic image measurement apparatus 76 such as CT apparatus or NMR apparatus is connected to the image processing apparatus through the interface section 77.

The present invention is not limited to the aforementioned embodiments. The present invention also includes various modifications to be made within the scope of the claims annexed to and forming a part of this specification.

What is claimed is:

1. An image processing apparatus comprising:
   a memory for storing three-dimensional data;
   a table for allocating color information so as to correspond to voxel values;
   an operation section for generating a DRR (Digitally Reconstructed Radiograph) by interpolating voxel values on a ray irradiated from a radiation source and adding up color information along the ray, the color information being obtained by converting the interpolated voxel values based on said table; and
   a display unit for displaying said generated DRR image.

2. An image processing apparatus according to claim 1, wherein said operation section for generating said DRR includes means for setting a plane of said DRR so as to coincide with a plane including an isocenter.

3. An image processing apparatus according to claim 1, further comprising means for expressing said three-dimensional data using a standard deviation.

4. An image processing apparatus according to claim 1, wherein said operation section for generating said DRR includes means for projecting values of voxels towards said radiation source, the voxels being located opposite to said radiation source with respect to the plane of said DRR.

5. An image processing apparatus according to claim 1, wherein said operation section for generating said DRR includes means for setting a resolution of said DRR to a desired value.

6. An image processing apparatus according to claim 1, wherein said operation section for generating said DRR includes means for setting a sampling interval between voxels on a ray connecting said radiation source to a pixel of said DRR to a desired value.

7. An image processing apparatus according to claim 1, wherein said operation section for generating said DRR includes
   means for partially selecting pixels of said DRR and calculating values of the selected pixels, and
   means for reconstructing said DRRs using said partially calculated pixel values, wherein
      said display unit includes means for sequentially displaying said DRRs reconstructed by using said partially calculated pixel values.

8. An image processing apparatus according to claim 1, wherein the DRR includes a plurality of pixels; and
   wherein the operation section interpolates voxel values on respective rays connecting the pixels of the DRR and the radiation source, and adds up color information along the respective rays, the color information being obtained by converting the interpolated voxel values based on the table.

9. An image processing apparatus according to claim 1, further comprising means for converting the three-dimensional data into edge-processed three-dimensional data in which edges are enhanced, the edge-processed three-dimensional data being expressed as a standard deviation of the three-dimensional data.

10. An image processing apparatus comprising:
    a memory for storing three-dimensional data;
    an operation section for calculating a standard deviation of said three-dimensional data and then calculating a second version of three-dimensional data in which said three-dimensional data is expressed using the standard deviation,
    the operation section for generating a DRR (Digitally Reconstructed Radiograph) by interpolating voxel values of the second version of the three-dimensional data on a ray irradiated from a radiation source and adding up said voxel values interpolated along the ray; and
    a display unit for displaying said generated DRR.

11. An image processing apparatus according to claim 10, wherein said operation section for generating said DRR includes means for setting a plane of said DRR so as to coincide with a plane including an isocenter.

12. An image processing apparatus according to claim 10, wherein said operation section for generating said DRR includes means for projecting values of voxels towards said radiation source, the voxels being located opposite to said radiation source with respect to the plane of said DRR.

13. An image processing apparatus according to claim 10, wherein said operation section for generating said DRR includes means for setting a resolution of said DRR to a desired value.

14. An image processing apparatus according to claim 10, wherein said operation section for generating said DRR includes means for setting a sampling interval between voxels on a ray connecting said radiation source to a pixel of said DRR to a desired value.

15. An image processing apparatus according to claim 10, wherein said operation section for generating said DRR includes
    means for partially selecting pixels of said DRR and calculating values of the selected pixels, and
    means for reconstructing said DRRs using said partially calculated pixel values, wherein
       said display unit includes means for sequentially displaying said DRRs reconstructed by using said partially calculated pixel values.

16. An image processing apparatus according to claim 10, wherein the DRR includes a plurality of pixels; and
    wherein the operation section interpolates voxel values on respective rays connecting the pixels of the DRR and the radiation source, and adds up the interpolated voxel values along the respective rays.

17. An image processing apparatus according to claim 10, wherein the second version of the three-dimensional data is edge-processed three-dimensional data in which edges are enhanced, the edge-processed three-dimensional data being expressed as the standard deviation of the three-dimensional data.

18. An image processing apparatus according to claim 10, wherein the three-dimensional data includes a plurality of voxel values representing values of a plurality of voxels in a three-dimensional space;
    wherein the second version of the three-dimensional data includes a plurality of voxel values representing values of the plurality of voxels in the three-dimensional space;
    wherein the voxel values of the second version of the three-dimensional data are standard deviations of the voxel values of the three-dimensional data; and wherein the operation section generates the DRR by interpolating voxel values of the second version of the three-dimensional data on the ray irradiated from the radiation source and adding up the interpolated voxel values along the ray.

19. An image processing method comprising:
a step of generating three-dimensional data;
a step of setting radiation conditions;
a step of setting a table for allocating color information so as to correspond to voxel values;
a step of interpolating voxel values on a ray irradiated from a radiation source;
a step of generating a DRR (Digitally Reconstructed Radiograph) by adding up color information along said ray, the color information being obtained by converting the interpolated voxel values based on said table; and
a step of displaying said DRR generated.

20. An image processing method according to claim 19, wherein said step of generating said DRR includes a step of setting a plane of said DRR so as to coincide with a plane including an isocenter.

21. An image processing method according to claim 19, further comprising a step of expressing said three-dimensional data by calculating a standard deviation.

22. An image processing method according to claim 19, wherein said step of generating said DRR includes a step of projecting values of voxels towards said radiation source, the voxels being located opposite to said radiation source with respect to the plane of said DRR.

23. An image processing method according to claim 19, wherein said step of generating said DRR includes a step of setting a resolution of said DRR to a desired value.

24. An image processing method according to claim 19, wherein said step of generating said DRR includes a step of setting a sampling interval between voxels on a ray connecting said radiation source to a pixel of said DRR to a desired value.

25. An image processing method according to claim 19, wherein said step of generating said DRR includes
a step of partially selecting pixels of said DRR and calculating values of the selected pixels, and
a step of reconstructing said DRRs using said partially calculated pixel values, wherein
said step of displaying includes a step of sequentially displaying said DRRs reconstructed by using said partially calculated pixel values.

26. An image processing method according to claim 19, wherein the DRR includes a plurality of pixels;
wherein the step of interpolating voxel values includes a step of interpolating voxel values on respective rays connecting the pixels of the DRR and the radiation source; and
wherein the step of generating a DRR includes a step of adding up color information along the respective rays, the color information being obtained by converting the interpolated voxel values based on the table.

27. An image processing method according to claim 19, further comprising a step of converting the three-dimensional data into edge-processed three-dimensional data in which edges are enhanced, the edge-processed three-dimensional data being expressed as a standard deviation of the three-dimensional data.

28. An image processing method comprising:
a step of generating three-dimensional data;
a step of calculating a second version of three-dimensional data by calculating a standard deviation of said three-dimensional data;
a step of setting radiation conditions;
a step for interpolating voxel values of the second version of the three-dimensional data, on a ray irradiated from a radiation source;
a step of generating a DRR (Digitally Reconstructed Radiograph) by adding up the voxel values interpolated along said ray; and
a step of displaying said DRR generated.

29. An image processing method according to claim 28, wherein said step of generating said DRR includes a step of setting a plane of said DRR so as to coincide with a plane including an isocenter.

30. An image processing method according to claim 28, wherein said step of generating said DRR includes a step of projecting values of voxels towards said radiation source, the voxels being located opposite to said radiation source with respect to the plane of said DRR.

31. An image processing method according to claim 28, wherein said step of generating said DRR includes a step of setting a resolution of said DRR to a desired value.

32. An image processing method according to claim 28, wherein said step of generating said DRR includes a step of setting a sampling interval between voxels on a ray connecting said radiation source to a pixel of said DRR to a desired value.

33. An image processing method according to claim 28, wherein said step of generating said DRR includes
a step of partially selecting pixels of said DRR and calculating values of the selected pixels, and
a step of reconstructing said DRRs using said partially calculated pixel values, wherein
said step of displaying includes a step of sequentially displaying said DRRs reconstructed by using said partially calculated pixel values.

34. An image processing method according to claim 28, wherein the DRR includes a plurality of pixels;
wherein the step of interpolating voxel values includes a step of interpolating voxel values on respective rays connecting the pixels of the DRR and the radiation source; and
wherein the step of generating a DRR includes a step of adding up the interpolated voxel values along the respective rays.

35. An image processing method according to claim 28, wherein the second version of the three-dimensional data is edge-processed three-dimensional data in which edges are enhanced, the edge-processed three-dimensional data being expressed as a standard deviation of the three-dimensional data.

36. An image processing method according to claim 28, wherein the three-dimensional data includes a plurality of voxel values representing values of a plurality of voxels in a three-dimensional space;
wherein the second version of the three-dimensional data includes a plurality of voxel values representing values of the plurality of voxels in the three-dimensional space;
wherein the voxel values of the second version of the three-dimensional data are standard deviations of the voxel values of the three-dimensional data;
wherein the step for interpolating includes the step of interpolating voxel values of the second version of the three-dimensional data on the ray irradiated from the radiation source; and
wherein the step of generating includes the step of generating the DRR by adding up the interpolated voxel values along the ray.

* * * * *